United States Patent
Zhang et al.

(10) Patent No.: US 12,061,154 B2
(45) Date of Patent: Aug. 13, 2024

(54) METHOD FOR CONSTRUCTING RECOGNITION MODEL OF MOISTURE DAMAGE OF ASPHALT PAVEMENT AND METHOD AND SYSTEM FOR RECOGNIZING MOISTURE DAMAGE OF ASPHALT PAVEMENT

(71) Applicant: CHANG'AN UNIVERSITY, Xi'an (CN)

(72) Inventors: Jun Zhang, Xi'an (CN); Jun Tao, Xi'an (CN); Chao Zhang, Xi'an (CN)

(73) Assignee: CHANG'AN UNIVERSITY, Xi'an (CN)

( * ) Notice: Subject to any disclaimer, the term of this patent is extended or adjusted under 35 U.S.C. 154(b) by 379 days.

(21) Appl. No.: 17/631,453

(22) PCT Filed: Oct. 13, 2020

(86) PCT No.: PCT/CN2020/120601
§ 371 (c)(1),
(2) Date: Jan. 29, 2022

(87) PCT Pub. No.: WO2021/174857
PCT Pub. Date: Sep. 10, 2021

(65) Prior Publication Data
US 2022/0276182 A1 Sep. 1, 2022

(30) Foreign Application Priority Data
Mar. 3, 2020 (CN) .......................... 202010140645.0

(51) Int. Cl.
*G01N 22/02* (2006.01)
*G01N 33/24* (2006.01)
(Continued)

(52) U.S. Cl.
CPC ............. *G01N 22/02* (2013.01); *G01N 33/24* (2013.01); *G06F 18/214* (2023.01); *G06N 3/04* (2013.01);
(Continued)

(58) Field of Classification Search
CPC ...... G01N 22/02; G01N 33/24; G06F 18/214; G06F 2218/12; G06N 3/04
(Continued)

(56) References Cited

U.S. PATENT DOCUMENTS

| 5,835,053 | A | * | 11/1998 | Davis | G01S 13/0209 |
| | | | | | 342/22 |
| 2019/0301109 | A1 | * | 10/2019 | Roberts | G01S 13/885 |
| 2022/0276374 | A1 | * | 9/2022 | Zhang | G01S 13/885 |

FOREIGN PATENT DOCUMENTS

| CN | 107238821 A | 10/2017 |
| CN | 109782274 A | 5/2019 |

(Continued)

*Primary Examiner* — Aditya S Bhat
(74) *Attorney, Agent, or Firm* — Bayramoglu Law Offices LLC

(57) ABSTRACT

A method for constructing a recognition model of a moisture damage of an asphalt pavement, and a method and system for recognizing the moisture damage of the asphalt pavement are provided. The method includes the following steps: S1, acquiring an initial dataset through a Ground Penetrating Radar (GPR) pavement field survey; S2, acquiring a time-frequency image set; S3, adjusting a resolution of a time-frequency image; and S4, constructing the recognition model and recognizing the moisture damage of the asphalt pavement with the recognition model. —A method and a system for recognizing the moisture damage of the asphalt pavement are further provided. The method for constructing and the method and the system for recognizing solves a technical problem of detecting the moisture damage of the asphalt pavement automatically to not only improving a (Continued)

precision of a moisture damage recognition, but also providing a novel method for analyzing GPR original data.

8 Claims, 10 Drawing Sheets

(51) Int. Cl.
 *G06F 18/214* (2023.01)
 *G06N 3/04* (2023.01)
(52) U.S. Cl.
 CPC ...... *G06F 2218/02* (2023.01); *G06F 2218/12* (2023.01)
(58) Field of Classification Search
 USPC .......................................................... 702/35
 See application file for complete search history.

(56) References Cited

FOREIGN PATENT DOCUMENTS

| | | | |
|---|---|---|---|
| CN | 110458028 | A | 11/2019 |
| CN | 110552281 | A | 12/2019 |
| CN | 110736985 | A | 1/2020 |
| CN | 111476088 | A | 7/2020 |
| EP | 2985309 | A3 | 7/2016 |

* cited by examiner

METHOD FOR CONSTRUCTING RECOGNITION MODEL OF MOISTURE DAMAGE OF ASPHALT PAVEMENT AND METHOD AND SYSTEM FOR RECOGNIZING MOISTURE DAMAGE OF ASPHALT PAVEMENT

CROSS REFERENCE TO THE RELATED APPLICATIONS

This application is the national stage entry of International Application No. PCT/CN2020/120601, filed on Oct. 13, 2020, which is based upon and claims priority to Chinese Patent Application No. 202010140645.0 filed on Mar. 3, 2020, the entire contents of which are incorporated herein by reference.

TECHNICAL FIELD

The present invention belongs to the field of road maintenance, and relates to detection of moisture damage of asphalt pavements, in particular to a method for constructing a recognition model of a moisture damage of an asphalt pavement, and a method and system for recognizing the moisture damage of the asphalt pavement.

BACKGROUND

Ground penetrating radar (Ground Penetrating Radar, GPR) is an instrument for detecting a condition under the surface of earth and imaging by radar impulse waves, and its principle is detecting electromagnetic contrasts in a medium by emitting and receiving high frequency electromagnetic (EM) waves via an antenna. GPR uses a high frequency wireless radio wave which is usually polarized, the EM wave is emitted under the surface of the earth, and when the EM wave strikes an object buried under the surface of the earth or reaches a boundary with variable dielectric constants, a reflected wave received by the antenna will record a signal difference of a reflection echo. As GPR has the characteristics of high precision, high efficiency and non-destructive detection, GPR has already been applied to road maintenance, for example, GPR has been widely applied to cavitation of a tunnel substrate, pavement cavitation, recognition of dowel steel or a reinforcing bar of a building or a bridge deck slab and underground pipelines. Due to the difficulty in GPR data explanation, current GPR analysis depends on human analysis, which is both in time-wasting and labor-wasting. In particular, as a result of long highway mileage, it is hard to meet an intelligent detection demand for pavement maintenance with current artificial experience recognition method. Therefore, it is an urgent need for intelligent analysis and recognition method of the GPR signal.

Taking a common pavement defect as an example, the moisture damage is one of major reasons which cause early damage of the asphalt pavement. The moisture damage will damage strength and durability of an asphalt aggregate, which causes obvious defects of the asphalt pavement such as looseness, longitudinal and transverse cracks, upheavals, slurry pumping or whitening, pot holes and peeling of an asphalt layer, such that the service life of the pavement is lowered and the traffic safety is affected. Asphalt pavements in China have surpassed 4000 thousand km, such that it is of great significance to guarantee the traffic safety by quick detection of the moisture damage.

With development of computer technology and artificial intelligence (for example, deep learning), target detection based on GPR image has been applied to ground penetrating radar, for example, reinforcing steel bar detection with a hyperbola characteristic. Recognition based on GPR image needs an intense measurement to obtain a high quality image, which cannot meet the defect detection demand with traffic speed vehicle-mounted GPR system. Aiming at the problem, the patent application (a method for recognizing a moisture damage based on a time-frequency statistic characteristic of a ground penetrating signal 201910100046.3) is provided by the writer. A method for detecting the moisture damage based on a GPR signal is realized by statistical analysis through parameters of a time domain and a frequency domain, and meanwhile, the moisture damage and the normal pavement are different in time domain and frequency domain.

Wavelet analysis has an ability of representing a local characteristic of the signal in time and frequency domains and has the characteristic that by self-adaption, a low frequency signal changes slowly and a high frequency signal changes quickly, which can suppress noises effectively. Continuous wavelet transform (CWT) can represent a frequency component and a time interval corresponding to moisture damage and can explain a transmission characteristic of the GPR signal energy in the asphalt pavement. By means of its time-frequency characteristic diagram, the method has rich characteristics and further can realize automatic detection of the moisture damage more accurately.

SUMMARY

Aiming at deficiencies and defects in the prior art, the present invention aims to provide a method for constructing a recognition model of a moisture damage of an asphalt pavement, and a method and system for recognizing the moisture damage of the asphalt pavement. The technical problem that it is hard to detect the moisture damage of the asphalt pavement automatically in the prior art is solved.

In order to solve the technical problem, the present invention adopts a technical scheme as follows:

A method for constructing a recognition model of a moisture damage of an asphalt pavement, including the following steps:

S1, pre-processing a GPR pavement investigation data set to obtain an initial data set with a moisture damage, a bridge joint and a normal pavement;

S2, performing continuous wavelet transform on the initial data set by using continuous wavelet transform, and taking an amplitude of wavelet transform to construct a first time-frequency image data set;

S3, filtering a image in the first time-frequency image set to obtain a second time-frequency image so as to construct a second time-frequency image data set;

S4, performing normalization processing on the image in the second time-frequency image data set to obtain a third time-frequency image so as to construct a third time-frequency image data set, and tagging a moisture damage classification label for the image of the third time-frequency image data set; and S5, constructing the recognition model:

training a preconstructed GPRMCNN deep learning model to obtain a trained recognition model by taking the third time-frequency image data set as input data and the moisture damage classification label as output data;

wherein the GPRMCNN deep learning model adopts 16 layers of convolutional neural networks, comprising three convolutional layers and one full connecting layer, the size of a convolution kernel used by a convolutional operation is 3*3, down sampling is arranged behind the previous two convolutional layers and the last convolutional layer does not have a pool layer of down sampling and is connected to the full connecting layer through a Drop network.

The present invention further has the technical characteristics that

Further, in the field data acquisition process in the step 1, a sampling frequency is 10-20 times of a main frequency of an antenna.

Further, pre-processing procedure of GPR data includes removing direct current (DC) offset algorithm (to subtract the DC drift), static correction algorithm (to cut the air layer and correct the layer of asphalt pavement), a background removal algorithm, a band-pass filtering algorithm and a sliding average algorithm.

Further, in the step 5, a dimension size of the input data is 28*28 and the classification label is a number, wherein the normal pavement is 0, the bridge joint is 1 and the moisture damage is 2.

Further, the present invention provides a method for constructing a recognition model of a moisture damage of an asphalt pavement, including the following steps:

S51, pre-processing a GPR pavement investigation data set to obtain an initial data set with a moisture damage, a bridge joint and a normal pavement;

S52, acquiring a time-frequency image data set;

S53, inputting the time-frequency image data set into the recognition model according to claim 1 to obtain a moisture damage recognition result.

Further, the present invention further provides a system for recognizing a moisture damage of an asphalt pavement, including a data acquisition and pre-processing module and the recognition model according to claim 1, wherein the data acquisition and pre-processing module and the recognition module is used for pre-processing a dataset acquired by GPR pavement investigation to obtain a time-frequency image data set; and the recognition module is used for recognizing a moisture damage of an asphalt pavement to output a damage result.

Compared with the prior art, the present invention has the benefits that (1) The time-frequency diagram in a radar wave signal is extracted by adopting CWT method, so that classification on the moisture damage and the normal pavement can be achieved effectively, and meanwhile, the depth of the defect is further judged according to an energy distribution position in the time-frequency diagram;

(2) The filtered time-frequency diagram is directly used for constructing a classification model which includes comprehensive information of time domain and frequency domain, which avoids a defect that a conventional method of searching for time-frequency characteristic parameter dependent on a statistic method is incomplete in characteristic; and (3) The constructed moisture damage classification model can directly analyze a GPR initial signal (A-Scan signal), which avoids the demand on a sampling interval by existing GPR image (B-Scan) recognition, and designed GPRMCNN can provide a ground for intelligent application of vehicle-mounted large-scaled pavement defect investigation.

Further description of specific embodiments of the present invention in detail will be made below in combination with drawings.

DETAILED DESCRIPTION OF THE EMBODIMENTS

Specific embodiments of the present invention are given below. It should be noted that the present invention is not limited to the specific embodiments below and equivalent transformations made based on the technical scheme of the application shall fall within the scope of protection of the present invention.

Embodiment 1

The number of samples (A-Scan sample, single radar trace, or waveform) selected in the embodiment is 22453, wherein the number of the moisture damage samples is 8215, the number of the normal pavement samples is 8215 and the number of the bridge joint samples is 6023.

Figure 1:
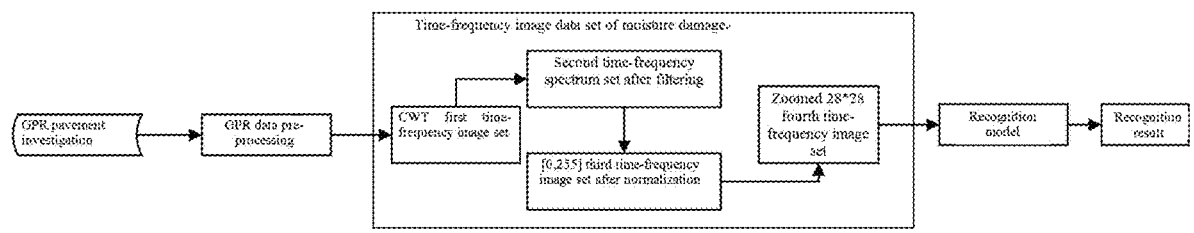
FIG. 1 is a recognition flow diagram according to the embodiment I of the present invention.
Figure 2:
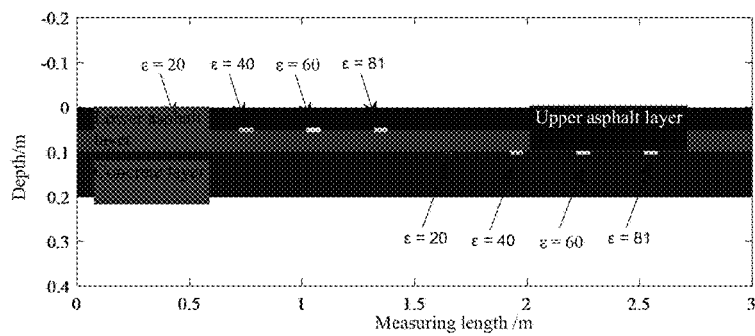
FIG. 2 is a model diagram of a simulated pavement.

The embodiment provides a method for recognizing a moisture damage of an asphalt pavement as shown in the FIG. 1. The method includes the steps:

S1, a GPR field survey data set is pre-processed to obtain an initial data set with a moisture damage, a bridge joint and a normal pavement, wherein in the field data collection process, a moisture damaged region of the pavement is marked in GPR acquisition software, and in the embodiment, a region with slurry pumping (stripping) or whitening in the pavement is marked;

these markers will emerge above the GPR B-Scan image (stacked of A-Scans) in form of small squares. In the FIG. 4, the markers of the typical GPR image of the field test of the asphalt pavement are "□", and the lower sides of the markers correspond to the moisture damage defect region. The moisture features corresponding to the markers as true values of moisture damage are used for determining characteristics of the moisture damage defect in GPR image.

In the field data acquisition process, a sampling frequency is 10-20 times of a central frequency of an antenna.

Pre-processing procedure of GPR data includes removing direct current (DC) offset algorithm (to subtract the DC drift), static correction algorithm (to cut the air layer and correct the layer of asphalt pavement), a background removal algorithm, a band-pass filtering algorithm and a sliding average algorithm.

in the step 1, the contrast of the GPR image is ranged from 1.2 to 1.6, preferably 1.4 in the embodiment.

Figure 4:
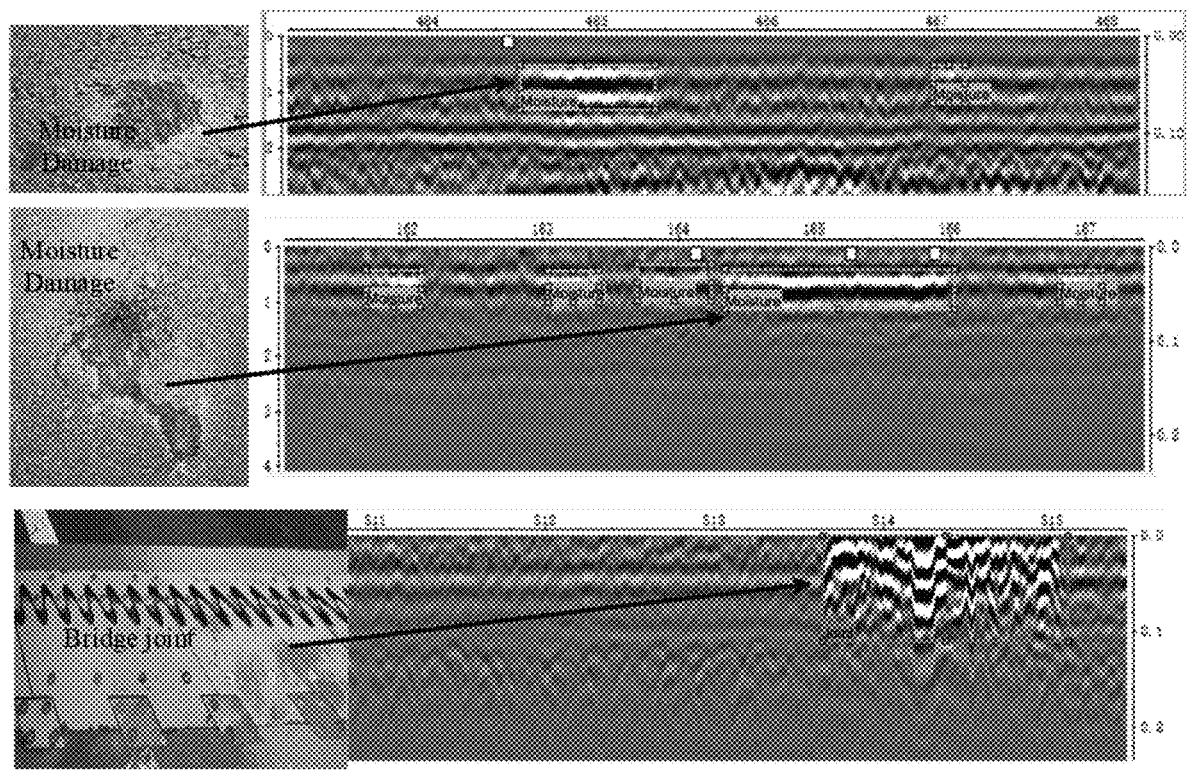
FIG. 4 is a typical GPRB-Scan image characteristic of a field test of the asphalt pavement.

FIG. 4 is the typical GPR image of the moisture damage data set of the embodiment, a field picture is on the left side, the corresponding GPR image is on the right side, and in a label, Moisture is the moisture damage and Joint is the bridge joint.

A process of acquiring the GPR data set of the moisture damage: when GPR antenna arrived at a observed whitening area, a marker of corresponding GPR traces will be recorded by data acquisition software, and main characteristics of the moisture damage are determined by plenty of investigation of living examples:

1) there are continuous or discontinuous highlighted regions in the asphalt;
2) the width/Height ratio in the image region is indefinite and is positively correlated to order of severity of the moisture damage.

The bottom image in the FIG. 4 is the bridge joint GPR image, which is characterized in that the bridge joint presents a continuous highlighted region from the pavement surface to certain depth and the continuous highlighted region is primarily different from the highlighted region of the moisture damage:

1) The characteristic is highlighted from the surface of the pavement downwards and hyperbola characteristics will emerge on two sides;
2) the highlighted region is continuous in characteristic and the depth from the surface to the lower side Depth is greater than or equal to 0.1 m;
3) the Width/Height ratio in the image region is smaller than 4 and the area Area is greater than 1000 pixel 2.

Figure 5A:
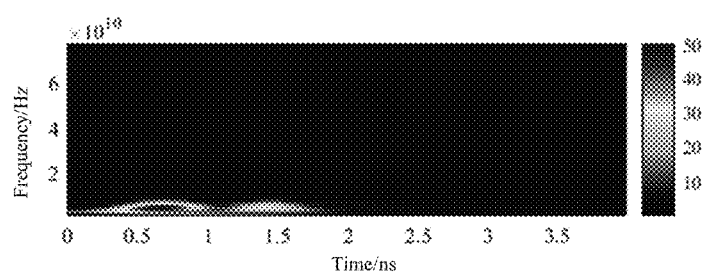
FIG. 5A is a normal pavement time-frequency comparison diagram of simulated data after continuous wavelet transform.
Figure 5B:
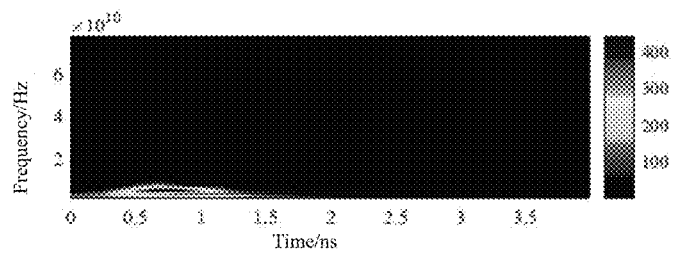
FIG. 5B is a 5 cm depth moisture damage time-frequency comparison diagram of simulated data after continuous wavelet transform.
Figure 5C:
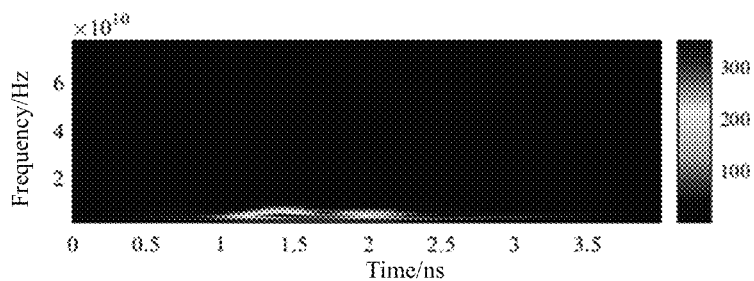
FIG. 5C is a 10 cm depth moisture damage time-frequency comparison diagram of simulated data after continuous wavelet transform.

S2, continuous wavelet transform is performed on the initial data set by using continuous wavelet transform, and an amplitude of wavelet transform taken construct a first time-frequency image data set;

as shown in FIGS. 5A-5C, normal pavement data and moisture damage data from the initial data set is transformed with continuous wavelet transform through a formula (1), wherein f(t) represents A-scan data of each sample in the initial data set, a is a scale factor, T is a time translation factor and t is a sampling time corresponding to the GPR signal f(t).

A continuous wavelet transform formula is as follows:

$$CWT_f(a, \tau) = [f(t), \varphi_{a,\tau}(t)] = 1/\sqrt{a} * \int f(t)\varphi^*\left(\frac{t-\tau}{a}\right)d(t) \quad (1)$$

$\varphi_{a,\tau}(t)$ in the (1) is a function of a mother wavelet j* after scaling and translating and is calculated by a formula (2):

$$\varphi_{a,\tau}(t) = \frac{1}{\sqrt{a}}\varphi^*\left(\frac{t-\tau}{a}\right), a, \tau \in R, a > 0, \quad (2)$$

wherein a is a scale factor, $\tau$ is a time translation factor and t is a time.

When |a| is smaller than 1, the mother wavelet j* (a function with a continuous property in the time domain and the frequency domain) is compressed and has a small supporting degree in a timer shaft, and corresponds to a high frequency because the mother wavelet is narrowed and changes quickly. On the contrary, when |a| is greater than 1, the mother wavelet is widened and changes slowly, and corresponds to a low frequency. The scale factor α represents stretching related to frequency.

Figure 14:
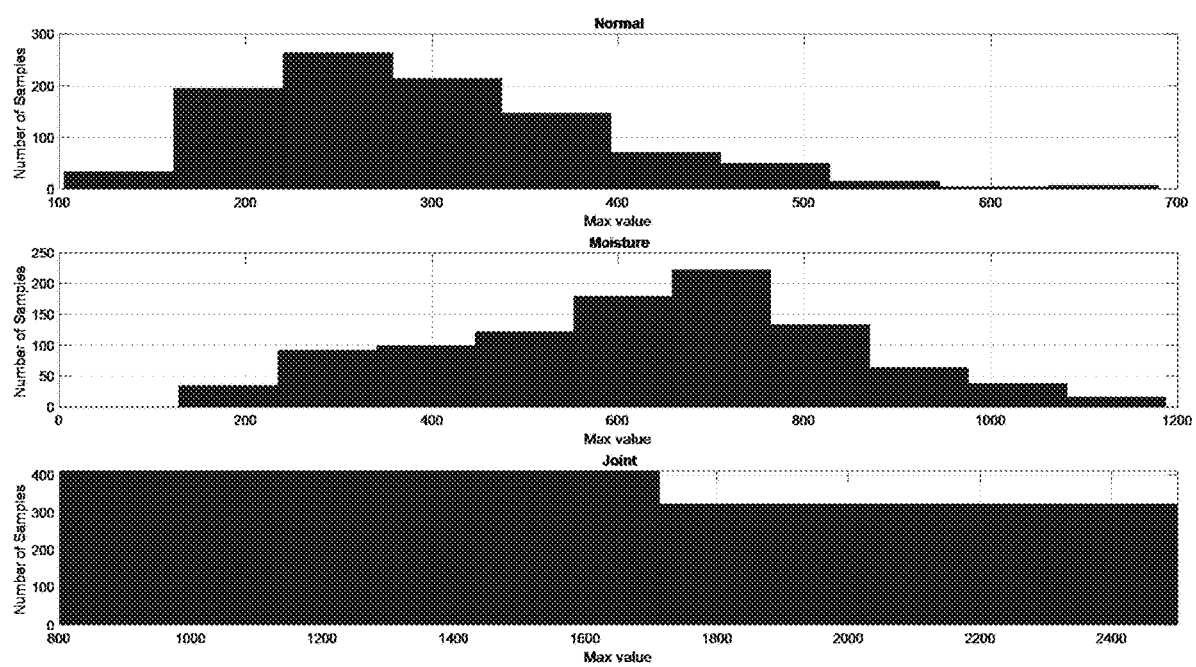
FIG. 14 is a CWT maximum value statistics distribution diagram of normal, moisture damage, and bridge joint samples in the embodiment 1.
Figure 15:
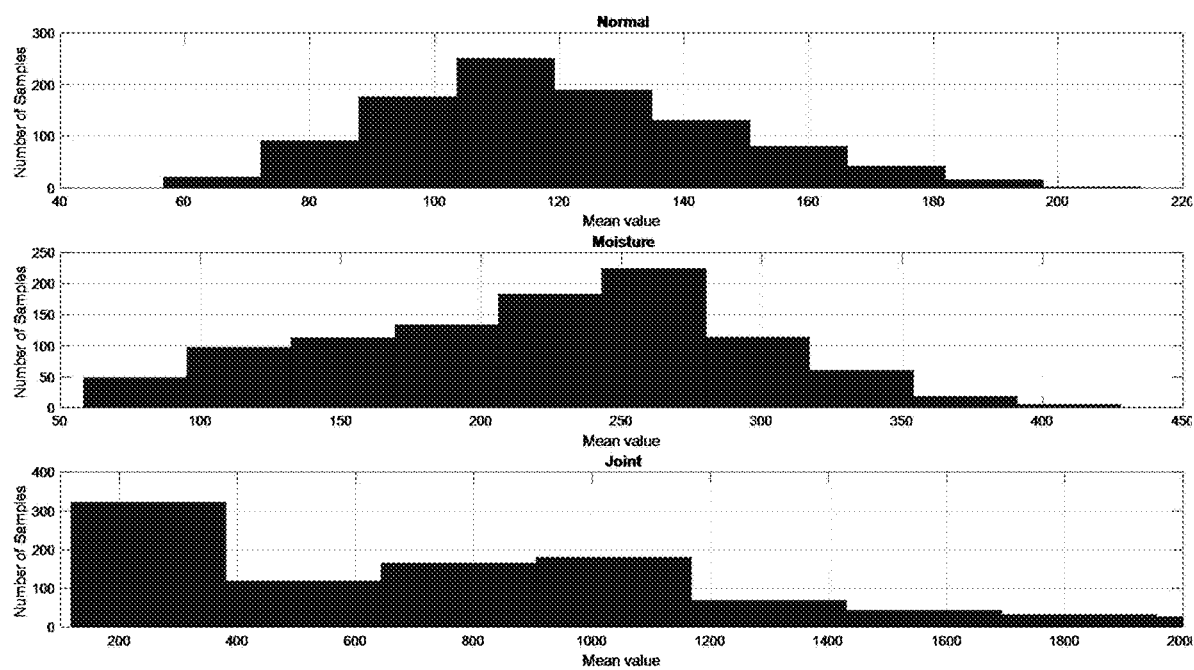
FIG. 15 is a CWT mean value statistics distribution diagram of normal, moisture damage, and bridge joint samples in the embodiment 1.

In the FIG. 14 and FIG. 15, the maximum value statistics distribution diagram of continuous wavelet transform and the mean value statistics distribution diagram of continuous wavelet transform of three samples used in the embodiment 1 are given respectively.

After continuous wavelet transform (CWT), the amplitude-frequency size of the array of the sample is 51*237 and the first time-frequency data set is constructed based on original samples.

Figure 3:
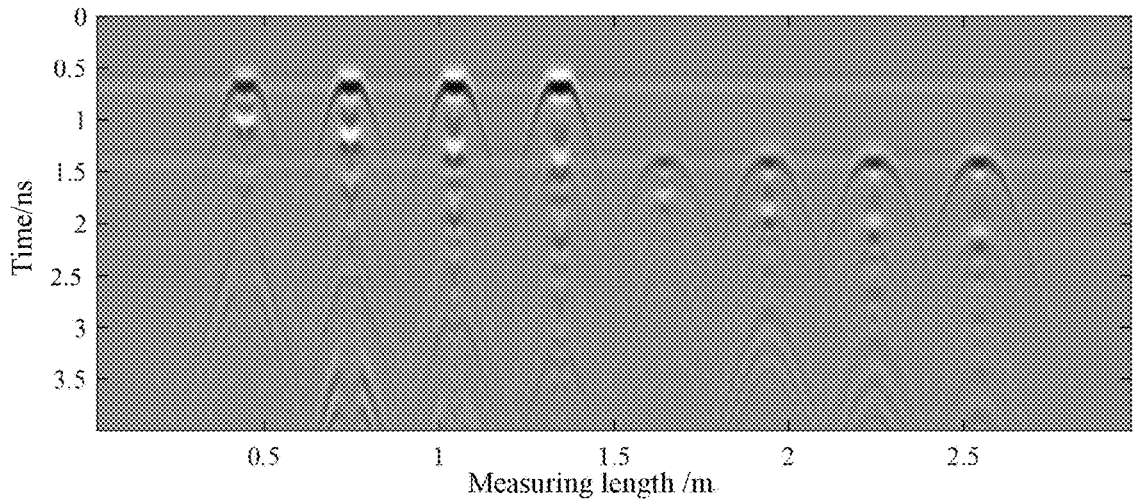
FIG. 3 is a GPR B-Scan image of the simulated pavement.

FIG. 3 is an image result schematic diagram of the simulated pavement. Data of the normal pavement and the moisture damage pavement is extracted from the diagram for CWT. FIGS. 5A-5C are the time-frequency comparison diagrams of the simulated data after CWT. It can be seen from FIGS. 5A-5C that the time-frequency energy (the maximum value of the time-frequency energy is 50) of the normal pavement is greatly different from those (the maximum value of the time-frequency energy is 400) of the pavements, the depth of the moisture damage of which is 5 cm and the depth of the moisture damage of which is 10 cm. Meanwhile, it can be known from the comparison diagrams of FIGS. 5B and 5C, in the diagram of FIG. 5B, the depth of the moisture damage of which is 5 cm, the time-frequency energy is concentrated at 0.5-1 ns; in the diagram of FIG. 5C, the depth of the moisture damage of which is 10 cm, the time-frequency energy is concentrated at 1.5-2 ns; and supposing the radar EM wave speed is calculated at 0.1 m/ns, the depth of the moisture damage is 0.25-5 cm. Therefore, the depth of the moisture damage defect affects the distribution position of the time-frequency energy, and the energy of the time-frequency diagram is concentrated at a defect depth, showing that the method not only can differentiate whether the pavement is normal or not, but also can locate the defect depth.

Figure 7A:
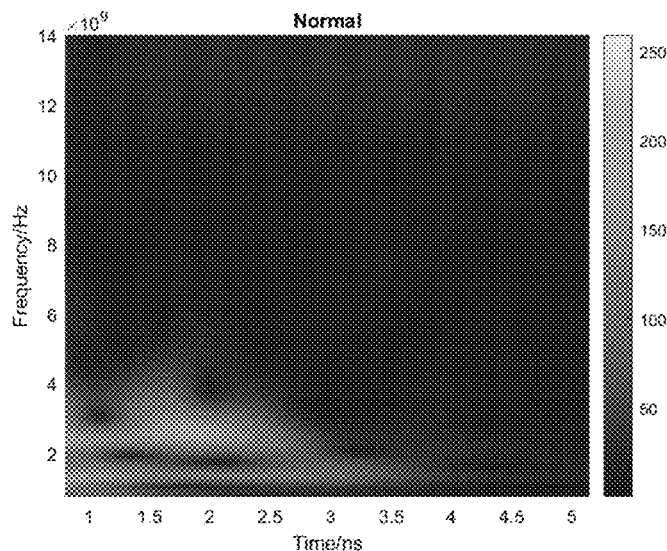
FIG. 7A is a first time-frequency diagram of the normal pavement of the actually measured data.
Figure 7B:
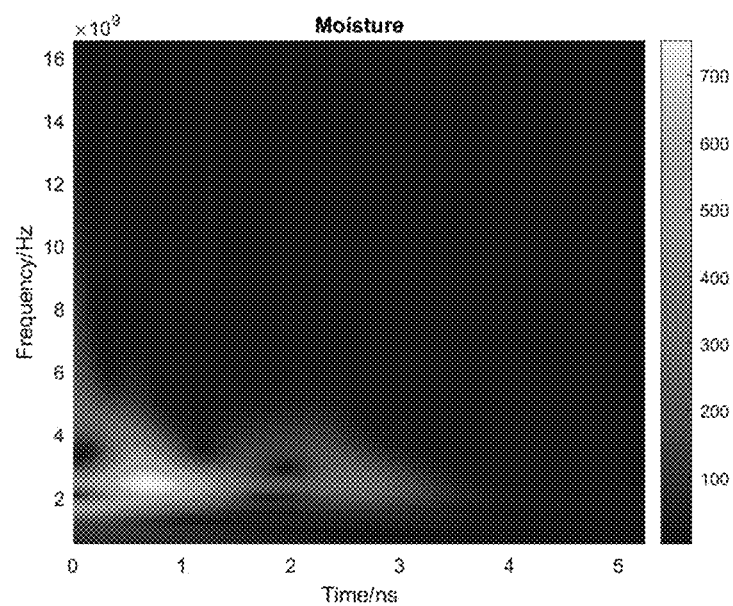
FIG. 7B is a first time-frequency diagram of the moisture damage pavement of the actually measured data.
Figure 7C:
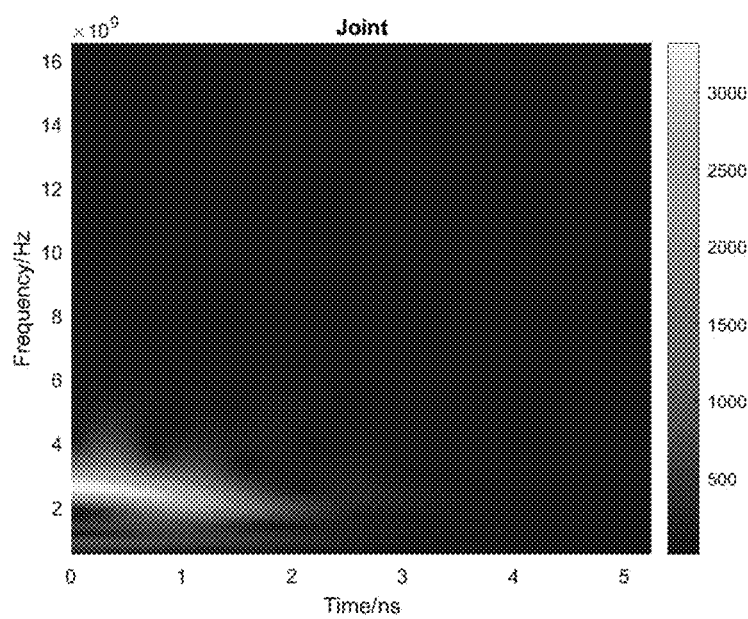
FIG. 7C is a first time-frequency diagram of the bridge joint of the actually measured data.
Figure 8A:
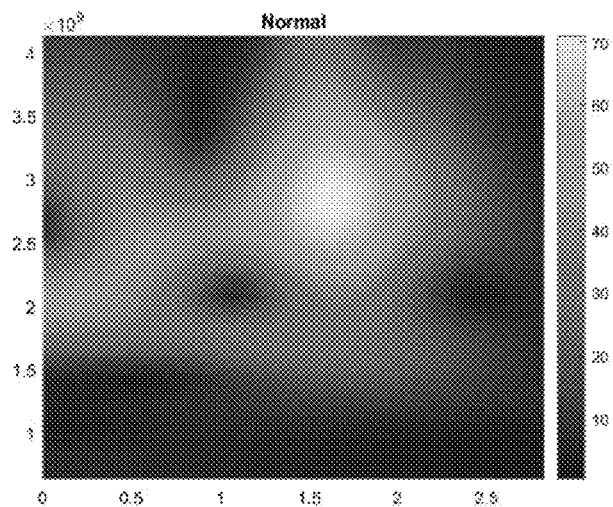
FIG. 8A is a second time-frequency diagram of the normal pavement.
Figure 8B:
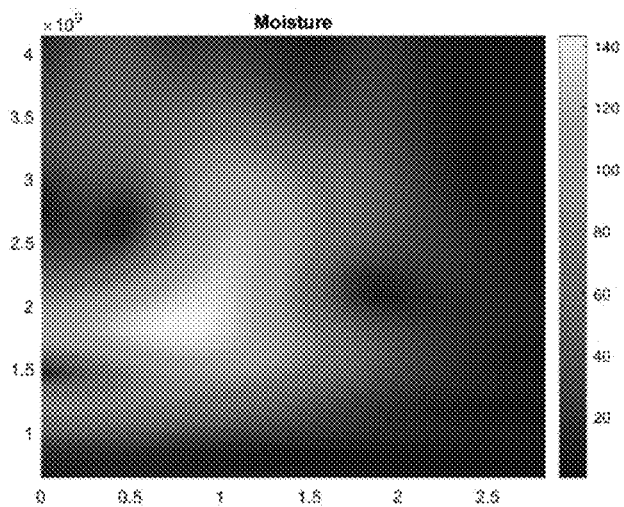
FIG. 8B is a second time-frequency diagram of the moisture damage pavement.
Figure 8C:
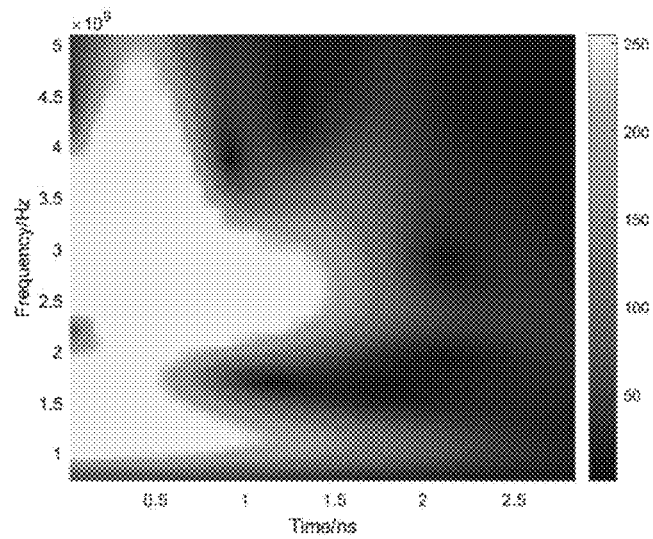
FIG. 8C is a second time-frequency diagram of the bridge joint.
Figure 9A:
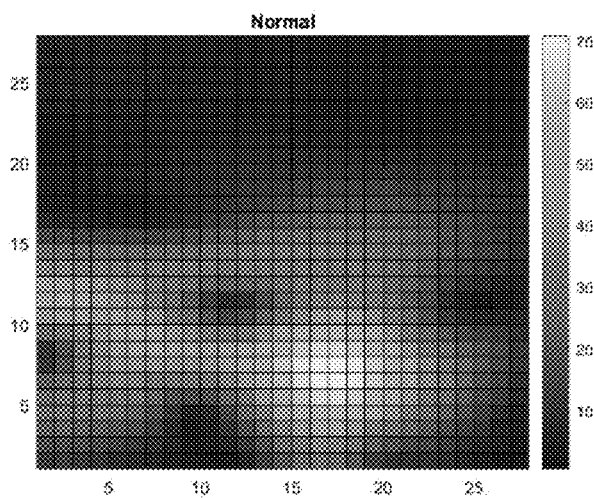
FIG. 9A is a fourth time-frequency diagram of the normal pavement.
Figure 9B:
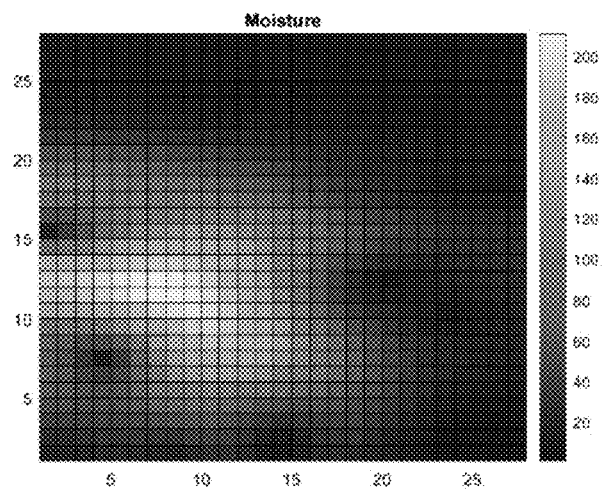
FIG. 9B is a fourth time-frequency diagram of the moisture damage pavement.
Figure 9C:
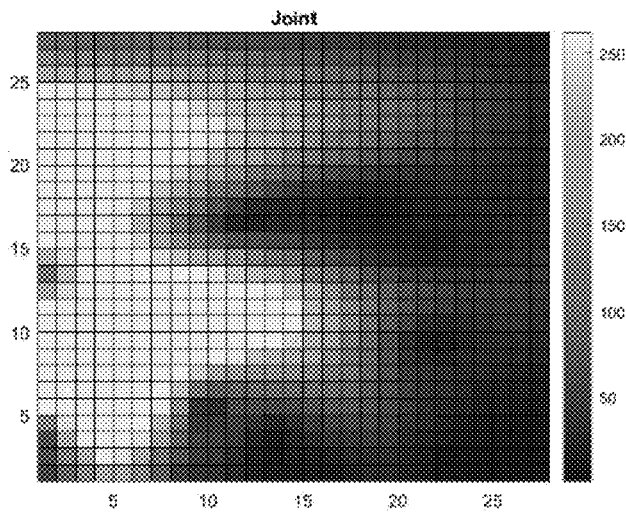
FIG. 9C is a fourth time-frequency diagram of the bridge joint.

FIGS. 7A-7C are comparison diagrams of the first time-frequency image of the actually measured data after CWT, wherein FIG. 7A is a time-frequency diagram of the normal pavement of the field survey data, FIG. 7B is a time-frequency of the moisture damage pavement of the field survey data and FIG. 7C is a time-frequency diagram of the bridge joint pavement of the field survey data. It can be known from FIGS. 7A-7C, a time-frequency energy comparison result is as follows: moisture damage is greater than normal pavement but smaller than bridge joint, so that the method can provide a ground for classification.

S3, a image in the first time-frequency image set is filtered to obtain a second time-frequency image so as to construct a second first time-frequency image data set;

it can be known from contrastive analysis, the energy of the three targets (Moisture damage-Moisture, Normal pavement-Normal and bridge joint-Joint) are concentrated at 0.4-4 GHz in frequency domain and 0-3 ns in the time domains a.

The time-frequency data is filtered by using Morse wavelet, and filtering parameters are data within a range of frequency domain [0.4-4 GHz] and time domain [0-3 ns] (corresponding to a sample at a A-scan sampling point [1,100]). After filtering processing, the amplitude-frequency size of the array of each sample after continuous wavelet transform (CWT) is reduced from 51*237 to 15*100, which is defined as the second time-frequency image set.

S4, normalization processing is performed on the image in the second time-frequency image set to obtain a third time-frequency image so as to construct a third time-frequency image set, and a moisture damage classification label is annotated for the image of the third time-frequency image set; and statistical analysis on the maximum value, the minimum value and the mean value is performed on the second time-frequency image, statistics on distribution proportion is performed, and a statistics result is as shown in the FIG. 14 and FIG. 15, a maximum value MaxCWT=1800 is determined, and normalization processing is performed on the second time-frequency image sample and the data is mapped to [0, 255].

Normalization processing specifically includes:

a sample matrix in the third time-frequency image data set is defined as A[m*n], the maximum value is defined as MaxCWT, and then steps are performed as follows:

The maximum value in the matrix A is defined, and if elements in the matrix exceed the maximum value, the value is assigned as the maximum value maxCWT and otherwise, the original value is reserved, and a calculating method of some point A(i,j) in the matrix specifically includes:

$$A(i,j) = \begin{cases} A(i,j), \text{ when } A(i,j) <= \text{Max}CWT \\ \text{Max}CWT, \text{ when } A(i,j) > \text{Max } CWT \end{cases} i \in [1,m], j \in [1,n] \quad (3)$$

The defined matrix A is normalized and is mapped to the range of [0, 255], and the calculating method is as follows:

$$A(i,j) = k \times A(i,j)/\text{MaxCWT, where } i \in [1,m], j \in [1,n] \quad (4)$$

wherein k is equal to 255 to map in the range of [0,255].

Normalization of the amplitude after continuous transform can be achieved according to the steps.

It is found by researches that image with different resolutions are different in accuracy in the recognition model, and the picture resolution affect a model recognition result directly. Therefore, as a preferred scheme, in the embodiment, the resolution of the third time-frequency image is adjusted: the third time-frequency image data set is zoomed to 28*28 directly to obtain a fourth time-frequency image data set;

a constructed GPRMCNN deep learning model is trained to obtain a trained recognition model by taking the zoomed 28*28 fourth time-frequency image set as input data and the moisture damage classification label as output data.

Figure 10:
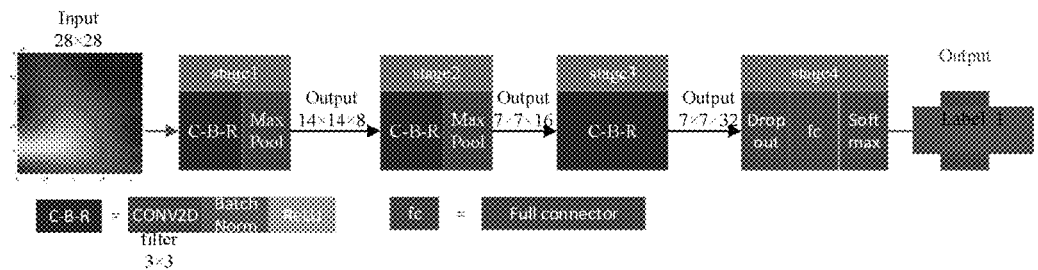
FIG. 10 is a structural schematic diagram of the recognition model of the present invention.

As shown in the FIG. 10, the GPRMCNN deep learning model adopts 16 layers of convolutional neural networks, including three convolutional layers and one full connecting layer, the size of a convolution kernel used by a convolutional operation is 3*3, down sampling is arranged behind the previous two convolutional layers and the resolution of the input picture is converted from 28*28 into 7*7*32, and the last convolutional layer does not have a pool layer of down sampling and is connected to the full connecting layer through a Drop network and the output layer is converted to 1*1*3.CNN original data is provided for follow-up GPRMCNN; Network parameters of the constructed GPRMCNN deep learning model are set as follows:

| Layer name | Output dimension | Parameter |
| --- | --- | --- |
| First layer | 14*14*8 | Conv: 3*3, 8, step 1 |
| | | BatchNorm: 1*1, 8 |
| | | maxpool: 2*2, step 2 |
| Second layer | 7*7*16 | Conv: 3*3, 16, step 1 |
| | | BatchNorm: 1*1, 16 |
| | | maxpool: 2*2, step 2 |
| Third layer | 7*7*32 | Conv: 3*3, 32, step 1 |
| | | BatchNorm: 1*1, 32 |
| | | drop out: 7*7*32, 20% |
| Fourth layer | 1*3 | fully connected: 1*1*3 |
| | | soft max: 1*1*3 |

The GPRMCNN deep learning model adopting the fourth time-frequency image set is divided into a training set, a test set and a verification set with the distribution proportion being 60%, 20% and 20%. A specific model training method includes training the designed mixed deep learning model by using a TL(Transfer Learning), wherein parameters are set as follows: 'InitialLearnRate':0.005, 'MaxEpochs':15, ValidationFrequency':30.

The classification label is a number, wherein the normal pavement is 0, the bridge joint is 1 and the moisture damage is 2.

The deep learning model uses a classification precision index to measure performance of the model.

Figure 11:
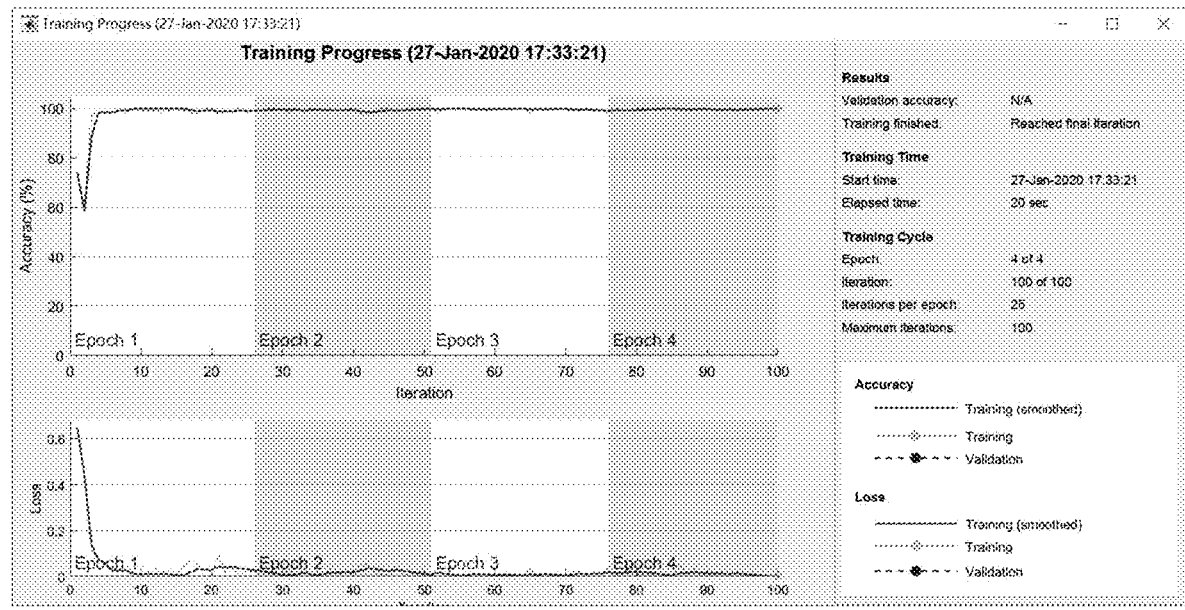
FIG. 11 is a training result diagram of the recognition model of the present invention.

FIG. 11 is a detection set result of the moisture damage and the normal pavement and the numbers of the collected moisture damage samples and normal samples are 1500. It can be known from FIG. 11 that recognition precisions of GPRMCNN on the moisture damage and the normal pavement reach 91.67% and 97.80% respectively, and the recognition precision of the bridge joint reaches 99.6%, showing that the classification precision is very high.

Figure 13:
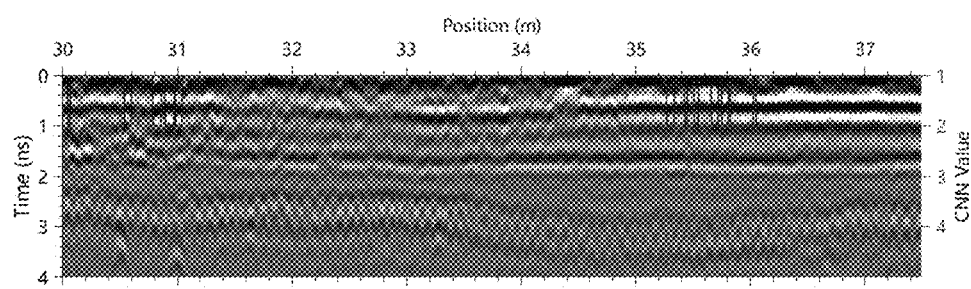
FIG. 13 is verification result diagram of actually measured data.

The classification result is drawn in an overlapped manner on the GPR image of pavement, the result is as shown in FIG. 13. It can be known form FIG. 13 that the detection model can recognize the moisture damage with the highlighted region in the GPR image correctly effectively, thereby the correctness of the method and the model is verified.

Comparative Example 1

Figure 6:
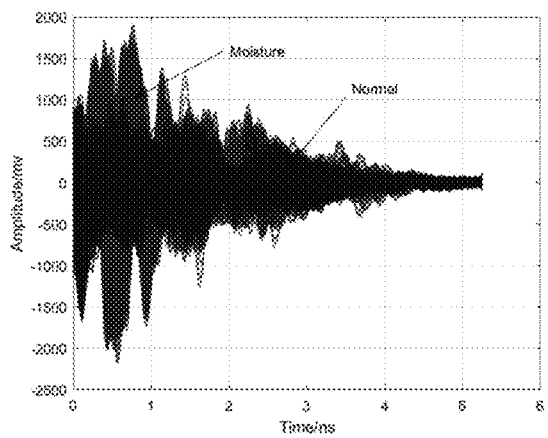
FIG. 6 is a time domain (A-scans) diagram of the moisture damage and the normal pavement in field survey

The comparative example provides the method for detecting the moisture damage of the asphalt pavement. Other steps of the method are same as those in the embodiment 1 and the difference is merely that filtering and normalization processing are not performed in the step 2. The initial data spectra are as shown in FIG. 4 and FIG. 6. The initial dimension of the time-frequency image is 51*237.51*237 data is zoomed in the step 3, and the model constructed by the method is defined as CNN with image.

The precision of model test is as shown in FIG. 11, the recognition precision of the moisture damage defect is 77.77% and the recognition precision of the normal pavement is 99.46%. The model can recognize the normal pavement well, while the recognition precision on the moisture damage defect is too low.

Comparative Example 2

The comparative example provides the method for detecting the moisture damage of the asphalt pavement. The method is as same as the embodiment I in step 1. The method adopting a conventional time-frequency characteristic extraction method constructs an ANN (artificial neural network, belonging to a machine learning method), the specific steps being as same as those of the method for recognizing the moisture damage based on the time-frequency statistics characteristic of the ground penetrating signal (the Chinese patent application number is 201910100046.3).

Figure 12:
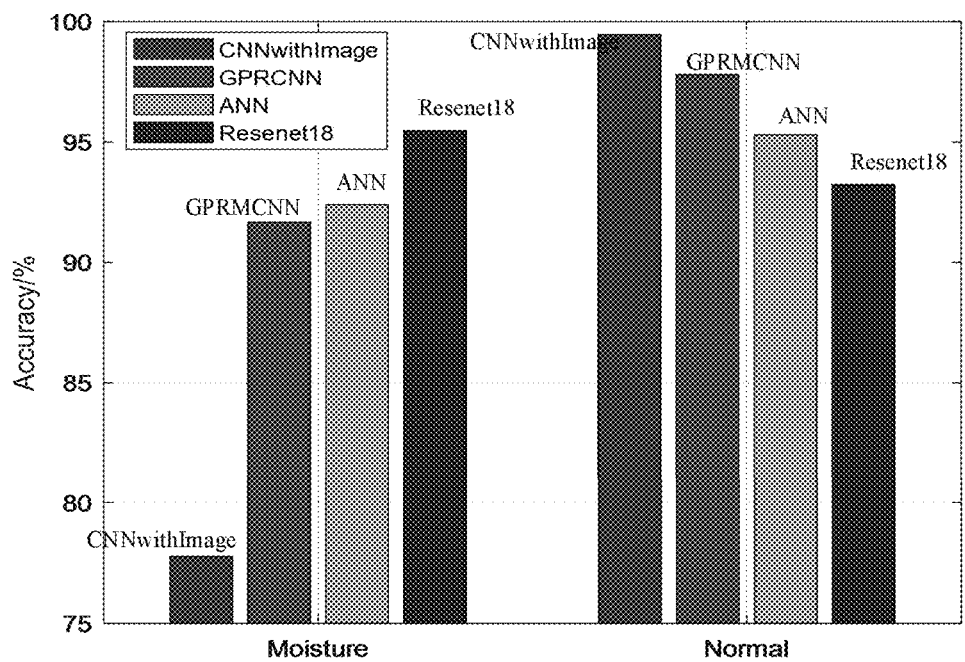
FIG. 12 is a recognition result comparison diagram of different recognition models.

The precision of model test is as same as ANN as shown in FIG. 12, wherein the recognition precision of the moisture damage is 92.4% and the recognition precision of the normal pavement is 95.3%. In comparison, on the test set, the overall precision of the GPRMCNN recognition model provided by the present invention is better, the recognition precision of the normal pavement is 2.5% higher and the recognition precision of the moisture damage is only 0.6% in difference. In view of higher proportion of the normal pavement in the actual pavement, the GPRMCNN recognition model is more excellent in recognition effect.

Comparative Example 3

The comparative example provides the method for detecting the moisture damage of the asphalt pavement. Other steps of the method are same as those in the embodiment 1 and the difference is merely that when the time-frequency image is zoomed, the time-frequency image is not stored as a 28*28 matrix but a 224*224 RGB picture; then the obtained time-frequency image is input to the Resenet18 directly, and the training parameters are set as 'Momentum', 0.9 and MiniBatchSize', 64, respectively.

The precision of the test result is as same as Resenet18 as shown in FIG. 12, wherein the recognition precision of the moisture damage on the test set is 95.47% and the recognition precision of the normal pavement is 93.23%. The training time of the model on a single CPU is 64 hours which is far longer than the times of GPRMCNN (1 h) and ANN (10 min). The recognition precision of the normal pavement is low and most actual pavements are normal pavements (95-99% of the pavements are normal pavements), such that the model precision is poorer than that of the GPRMCNN.

Contrastive analysis is performed on the embodiment 1, the comparative example 2 and the comparative example 3. FIG. 12 is the comparative results between the deep models and GPRMCNN recognition model. It is found by comparison that in the precision of the sample test set, the recognition precision of the moisture damage is as follows: Resenet18 (95.47%) is greater than ANN (92.4%), the ANN (92.4%) is greater than GPRMCNN (91.67%), GPRMCNN (91.67%) is greater than CNN with image (77.77%) and the recognition precision of the normal pavement is as follows: CNN with image (99.46%) is greater than GPRMCNN (97.80%), GPRMCNN (97.80%) is greater than ANN (95.3%), ANN (95.3%) is greater than Resenet18 (93.23%). In total recognition precision evaluation, the precision of the GPRMCNN is more excellent, and the comparison result further verifies the accuracy of the method.

What is claimed is:

1. A method for constructing and using a recognition model of a moisture damage of an asphalt pavement, comprising the following steps:
   S1, pre-processing, using at least one computer processor, a Ground Penetrating Radar (GPR) pavement investigation data set, acquired via an antenna, to obtain an initial data set with the moisture damage, a bridge joint and a normal pavement;
   S2, performing, using the at least one computer processor, a continuous wavelet transform on the initial data set by using the continuous wavelet transform, and taking an amplitude of the continuous wavelet transform to construct a first time-frequency image data set;
   S3, filtering, using the at least one computer processor, a first time-frequency image in the first time-frequency image set to obtain a second time-frequency image to construct a second first time-frequency image data set;
   S4, performing, using the at least one computer processor, a normalization processing on the second time-frequency image in the second time-frequency image set to obtain a third time-frequency image to construct a third time-frequency image set, and tagging a moisture damage classification label for the third time-frequency image of the third time-frequency image set; and
   S5, constructing, using the at least one computer processor, the recognition model:
   training a preconstructed Ground Penetrating Radar Moisture Content Neural Network (GPRMCNN) deep learning model to obtain a trained recognition model by taking the third time-frequency image set as input data and the moisture damage classification label as output data,
   wherein the preconstructed GPRMCNN deep learning model adopts 16 layers of convolutional neural networks, comprising three convolutional layers and one full connecting layer, a size of a convolution kernel used by a convolutional operation is 3*3, a down sampling is arranged behind previous two convolutional layers and a last convolutional layer does not have a pool layer of the down sampling and is connected to the one full connecting layer through a Drop network;
   using the recognition model to recognize the moisture damage of the asphalt pavement; and
   outputting a damage result.

2. The method according to claim 1, wherein a data acquisition process in the S1 has a sampling frequency of 10-20 times of a main frequency of the antenna.

3. The method according to claim 1, wherein in the S1, a pre-processing procedure of GPR data comprises using a removing direct current (DC) offset algorithm to subtract a DC drift, using a static correction algorithm to cut an air layer and correct a layer of the asphalt pavement, using a background removal algorithm, using a band-pass filtering algorithm and using a sliding average algorithm.

4. The method according to claim 1, wherein in the S5, a dimension size of the input data is 28*28 and the moisture damage classification label is a number, wherein the normal pavement is 0, the bridge joint is 1 and the moisture damage is 2.

5. A method for recognizing a moisture damage of an asphalt pavement, comprising the following steps:

S51, pre-processing a GPR pavement investigation data set to obtain an initial data set with the moisture damage, a bridge joint and a normal pavement;

S52, acquiring a time-frequency image set; and

S53, inputting the time-frequency image set into a recognition model obtained by the method of claim 1 to obtain a moisture damage recognition result.

6. A system for recognizing a moisture damage of an asphalt pavement, comprising a data acquisition and pre-processing module and a recognition model obtained by the method of claim 1, the data acquisition and pre-processing module comprising executable code stored on a non-transitory storage medium and executable by the at least one computer processor, wherein the data acquisition and pre-processing module and the recognition model is used for pre-processing a dataset acquired by GPR pavement investigation to obtain a time-frequency image set; and the recognition model is used for recognizing the moisture damage of the asphalt pavement to output a damage result.

7. The method according to claim 1, wherein the preconstructed GPRMCNN deep learning model is applied as part of a vehicle-mounted large-scaled pavement defect investigation.

8. The method according to claim 1, wherein the preconstructed GPRMCNN deep learning model is configured to can directly analyze a GPR initial signal (A-Scan signal).

* * * * *